United States Patent [19]

Lamb et al.

[11] Patent Number: 4,488,896

[45] Date of Patent: Dec. 18, 1984

[54] METHODS AND COMPOSITIONS FOR THE SELECTIVE CONTROL OF UNDESIRABLE WEED SPECIES IN THE PRESENCE OF WET-LAND CROPS

[75] Inventors: Glentworth Lamb, Lawrenceville, N.J.; Feliciano B. Calora, Makati, Philippines

[73] Assignee: American Cyanamid Company, Stamford, Conn.

[21] Appl. No.: 228,641

[22] Filed: Jan. 26, 1981

Related U.S. Application Data

[63] Continuation-in-part of Ser. No. 129,962, Mar. 13, 1980, abandoned.

[51] Int. Cl.³ .................... A01N 43/50; A01N 33/02
[52] U.S. Cl. .......................................... 71/92; 71/121
[58] Field of Search ............................. 71/92, 121

[56] References Cited

U.S. PATENT DOCUMENTS

| | | | |
|---|---|---|---|
| 3,920,742 | 11/1975 | Lutz et al. | 71/121 |
| 3,933,467 | 1/1976 | Fischer | 71/121 |
| 4,123,250 | 10/1978 | Kupelian | 71/121 |
| 4,188,487 | 2/1980 | Los | 71/92 |
| 4,201,565 | 5/1980 | O'Neal | 71/92 |

*Primary Examiner*—Glennon H. Hollrah
*Attorney, Agent, or Firm*—Estelle J. Tsevdos; Alphonse R. Noë

[57] ABSTRACT

There is provided a novel method for treating wet-land crop growing areas so as to selectively control undesirable weed species in the presence of said wet-land crops and to simultaneously and synergistically enhance the crop yield therefrom utilizing herbicidal compositions containing as the active ingredients (a) N-(1-ethylpropyl)-2,6-dinitro-3,4-xylidine and (b) methyl-o-(5-isopropyl-5-methyl-4-oxo-2-imidazolin-2-yl)benzoate or sodium-o-(5-isopropyl-5-methyl-4-oxo-2-imidazolin-2-yl)benzoate.

3 Claims, No Drawings

METHODS AND COMPOSITIONS FOR THE SELECTIVE CONTROL OF UNDESIRABLE WEED SPECIES IN THE PRESENCE OF WET-LAND CROPS

This application is a continuation-in-part of Ser. No. 129,962, filed Mar. 13, 1980, now abandoned.

The present invention relates to a novel method for treating wet-land crop growing areas, particularly irrigated or flooded rice paddies, so as to selectively control weeds in said paddies while simultaneously increasing the rice yield from said treated paddies. More particularly, it relates to a method for the selective control of undesirable plant species in the presesence of rice crops and to the simultaneous enhancement of rice yield by applying to the growing area of drill seeded rice, 0 to 2 days following seeding, or to transplanted rice, 3 to 7 days after said crop is transplanted, from about 0.75 to about 1.75 kg/hectare of N-(1-ethylpropyl)-2,6-dinitro-3,4-xylidine and from about 0.5 to about 0.75 kg/hectare of methyl-o-(5-isopropyl-5-methyl-4-oxo-2-imidazolin-2-yl)benzoate or sodium-o-(5-methyl-4-oxo-2-imidazolin-2-yl)benzoate.

Still more particularly, this invention relates to a synergistic composition and/or method for enhancing rice yields from irrigated and flood rice paddies and for simultaneously controlling undesirable annual and perennial weeds therein. The composition and/or method involve the application to the growing area of drill seeded rice, 0 to 2 days following seeding a composition which provides from 0.75 to 1.75 kg/hectare and preferably 1.50 to 1.75 kg/hectare of N-(1-elthylpropyl)-2,6-dinitro- 3,4-xylidine and 0.05 to 0.75 kg/hectare of sodium-o-(5-isopropyl-5-methyl-4-oxo-2-imidazoline-2-yl)benzoate.

As is disclosed in U.S. Pat. No. 3,920,742, which is incorporated by reference herein, N-(1-ethylpropyl)-2,6-dinitro-3,4-xylidine is an effective preemergence herbicide useful for the control of certain undesirable monocotyledonous and dicotyledonous plant species. Patentees demonstrate selective control of weed species, such as crabgrass, velvet leaf, pigweed, lambsquarters, barnyard grass and green foxtail, in the presence of crop plants such as soybeans, cotton and corn. However, patentees do not disclose or contemplate weed control problems in wet-land crop areas and appear to be primarily concerned with the control of undesirable grass plants and broadleaf weeds which are of major economic importance in dry-land farming areas. With the exception of *Echinochloa Crus-galli* the crops and weeds utilized by the patentees and the procedures employed for herbicidal evaluations, all suggest utilization of the N-secondary alkyl-2,6-dinitro-3,4-xylidines for control of non-aquatic weeds and the protection of dry-land crops, i.e. crops which are not cultivated in an aqueous or wet environment. They do not suggest that N-(1-ethyproply)-2,6-dinitro-3,4-xylidine, alone or in combination with other chemical compositions, would be highly effective for the selective control of weed species indigenous to the wet-lands, such as *Monochoria vaginalis, Elatine triandra, Sagittaria pygmaea, Eleocharis acicularis, Scirpus hotarui, Cyperus serotinus, Jussiaea prostrata, Eclipta alba, Justicia procumbeus, Cyperus difformis, Rotala indica* and *Lindernia pyxidaria*, in the presence of wet-land crops such as rice.

In addition, it is known that methyl-o-(5-isopropyl-5-methyl-4-oxo-2-imidazolin-2-yl)benzoate and sodium-o-(5-isopropyl-5-methyl-4-oxo-2-imidazolin-2yl)benzoate are herbicidal agents as disclosed in Belgian Pat. No. 869,535, issued Feb. 5, 1979 and/or U.S. Pat. No. 4,188,487 issued Feb. 12, 1980. However, said patents are concerned with the control of undesirable weed species indigenous to dry-land farming regions. Although the patentee does include *Echinochloa crus-galli* and *Cyperus rotundus* L. in preemergence and postemergence herbicidal evaluations, there is no suggestion that said benzoate compounds could be used in combination with other herbicidal agents to selectively control undesirable wet-land weed species, while simultaneously and synergistically increasing the yield of wet-land crops, especially rice.

It is, therefore, surprising to find that irrigated or flooded rice paddies can be effectively treated with from about 0.75 to 1.75 kg/hectare of N-(1-ethylpropyl)-2,6-dinitro3,4-xylidine and from about 0.5 to 0.75 kg/hectare of methyl-o-(5-isopropyl-5-methyl-4-oxo-2-imidazolin-2-yl)benzoate or sodium-o-(5-isopropyl-5-methyl-4-oxo-2-imidazolin-2-yl)benzoate, to control both annual and perennial weeds and synergistically enhance rice yields therefrom. This treatment provides virtually complete control of *Drymaria cordata, Ludwigia suffruticosa, Polygonum acre, Portulaca oleracea, Commelina nudiflora, Monochoria vaginalis, Elatine triandra, Eleocharis acicularis, Lindernia pyxidaria, Rotala indica, Echinochloa crus-galli, Cyperus difformis, Jussiaea prostrata* and *Eclipta alba*, very good control of *Sagittaria pygmaea* and some control of *Cyperus serotinus* and *Scirpus hotarui*. It is even more surprising to find that the above-said treatment of rice paddies, 3 to 7 days after transplanting of the rice or 0 to 2 days after drill seeding of the rice, not only provides excellent weed control, but also provides markedly enhanced rice yields over untreated paddies. At the preferred application rates of 1 kg/ha of N-(1-ethylpropyl)-2,6-dinitro-3,4-xylidine and 0.5 kg/ha of methyl-o-(5-isopropyl-5-methyl-4-oxy-2-imidazolin-2-yl)benzoate, it is found that rice yields are increased as much as 18% over other combination treatments; it is also found that the most preferred treatment, which provides from 1.50 to 1.75 kg/ha of N-(1-ethylpropyl)-2,6-dinitro-3,4-xylidine and 0.5 kg/ha or sodium-o-(5-isopropyl-providing essentially complete weed control, also synergistically enhances rice yields.

While weed control problems of significant magnitude confront farmers in the dry-land crop cultivation areas of the world, these problems are dwarfed by the weed control problems encountered in the cultivation of crops in the rich alluvial muddy soils of the wet-lands.

The magnitude of the weed control problems encountered in wet-land crop cultivation is evidenced by the fact that a single weed species, such as *Echinochloa crusgalli* frequently produces, in the rich alluvial soils of the wet-lands, as much as 25 to 35 tons per hectare of this undesirable grass plant. When such proliferation of undesirable weeds occur in the presence of a cultivated crop, such as rice, harvesting becomes an almost insurmountable task and crop yields are generally severely reduced.

It is, therefore, an object of the present invention to provide herbicidal compositions and a method for treating wet-land crop locations to control and/or inhibit the growth of undesirable weeds in the presence of the crops while simultaneously enhancing the yield of said crops. It is a further object of this invention to provide methods and herbicidal compositions for the treatment of drill seeded rice and transplanted paddy rice to selectively inhibit the growth of weeds in presence of said rice and to simultaneously increase rice yields from said treated paddies.

As indicated above, the method of the present invention involves the application of from 0.75 to 1.75 kg/ha of N-(1-ethylpropyl)-2,6-dinitro-3,4-xylidine and from 0.5 to 0.75 kg/ha of methyl-o-(5-isopropyl-5-methyl-4-oxo-2-imidazolin-2-yl)benzoate or sodium-o-(5-isopropyl-5-methyl-4-oxo-2-imidazolin-2-yl)benzoate to rice paddies, 3 to 7 days after the rice has been transplanted or 0 to 2 days after the paddy has been drill seeded.

The above-identified chemicals may be applied separately as dilute aqueous dispersions of wettable powders, emulsifiable concentrates or flowable liquids or they may be tank mixed at the site of application and applied as a dilute aqueous combination spray. They may also be prepared as an emulsifiable concentrate containing both active ingredients and applied in the form of a dilute aqueous spray containing both ingredients. Alternatively, the active ingredients may be applied to sorptive or non-sorptive granules and applied as granular formulations.

In practice, it is generally preferred to employ an emulsifiable concentrate of the N-(1-ethylpropyl)-2,6-dinitro-3,4-xylidine.

A typical emulsifiable concentrate of this xylidine can be prepared by dissolving or dispersing about 20% to 50% by weight of the N-(1-ethylpropyl)-2,6-dinitro-3,4-xylidine in about 77% to 40% by weight of an aromatic solvent, preferably a heavy aromatic solvent, containing about 3% to 10% by weight of an anionic/nonionic emulsifying agent or mixture of anionic/nonionic emulsifying agents.

The heavy aromatic solvent should contain 60% to 100% aromatics, have a specific gravity, at 60°/60° F., between about 0.880 and 1.5 and have a mixed aniline point between 30° F. and 95° F.

Anionic-nonionic emulsifying agents are generally blends of polyalkoxy carboxylic acid esters and sulfonated oils, blends of oil-soluble sulfonates and polyoxyethylene ethers, blends of polyoxyethylene phenols and alkyl sulfate or blends of oil-soluble metal sulfonate and polyoxyethylene ethers. The methyl-o-(5-isopropyl-5-methyl-4-oxo-2-imidazolin-2-yl)benzoate and sodium-o-(5-isopropyl-5-methyl-4-oxo-2-imidazolin-2-yl)benzoate are generally prepared, for use in the present invention, as emulsifiable concentrates or wettable powders.

Typical emulsifiable concentrates of said benzoates are generally prepared by dissolving or dispersing about 20% to 50% by weight of the methyl-o-(5-isopropyl-5-methyl-4-oxo-2-imidazolin-2-yl)benzoate or sodium-o-(5-isopropyl-5-methyl-4-oxo-2-imidazolin-2-yl) benzoate in about 65% to 15% by weight of an organic solvent, 10% to 25% by weight of a heavy aromatic solvent and about 5% to 10% by weight of a nonionic emulsifying agent or mixture of nonionic emulsifying agents.

Organic solvents which may be used in these formulations include: cyclohexane, methylisobutylketone, isopherone and mesityloxide.

The heavy aromatic solvents that find utility in the preparation of the above-mentioned concentrates have a mixed aniline point between 30° F. and 95° F. and a specific gravity at 60°/60° F. between 0.880 and 1.5. They contain about 60% to 100% aromatics.

Nonionic emulsifiers that can be employed in the above-identified emulsifiable concentrates include: polyoxyethylene sorbitan monooleates, monolaurates, monostearates, trioleates or the like, polyethylene glycol ethers of linear alcohols; polyalkylene glycol ethers, alkylaryl polyethylene glycol ether and the like.

Wettable powders of the above-said benzoate can be prepared by grinding together about 25% to 65% by weight of methyl-o-(5-isopropyl-5-methyl-4-oxo-2-imidazolin-2-yl) benzoate or sodium-o-(5-isopropyl-5-methyl-4-oxo-2-imidazolin-2-yl)benzoate, about 72% to 25% by weight of a finely divided carrier such as attapulgite, kaolin or diatomaceous earth, about 2% to 5% by weight of an anionic dispersant such as a highly purified sodium lignosulfonate or a sugar free, sodium-based sulfonate of Kraft lignin, and from 1 to 5% by weight of an anionic dispersant such as sodium N-methy-N-oleoyltaurate, alkyl phenoxy polyoxyethylene ethanol or sodium alkyl naphthalene sulfonate.

An emulsifiable concentrate, containing both N-(1-ethylpropyl)-2,6-dinitro-3,4-xylidine and methyl-o-(5-isopropyl-5-methyl-4-oxo-2-imidazolin-2-yl)benzoate or sodium-o-(5-isopropyl-5-methyl-4-oxo-2-imidazolin-2-yl)benzoate can be prepared by dissolving or dispersing about 20% to 30% by weight of the above-said xylidine and about 10% to 15% by weight of the above-said benzoate in about 30% to 20% by weight of cyclohexanone, methyl isobutyl ketone, isopherone or mesityl oxide, and about 35% to 25% by weight of a heavy aromatic solvent such as previously described in other formulations. To the thus prepared solution or dispersion is added from about 5% to 10% by weight of a nonionic/anionic emulsifying and/or dispersing agent or mixture of agents.

A typical emulsifiable concentrate formulation comprises the following: 25% by weight of N-(1-ethylpropyl)-2,6-dinitro-3,4-xylidine; 12.5% by weight of methyl-o-(5-isopropyl-5-methyl-4-oxo-2-imidazolin-2-yl)benzoate or the sodium-o-(5-isopropyl-5-methyl-4-oxo-2-imidazolin-2-yl)benzoate; 25% by weight of cyclohexanone; 30% by weight of PANASOL AN-2 heavy aromatic solvent; 2.5% by weight of Atlox 3403-F, anionic/nonionic emulsifier and 5% by weight of Atlox 3404-F emulsifier.

The Atlox emulsifiers are anionic/nonionic emulsifiers marketed by I.C.I. United States Inc.

PANASOL AN-2 is a heavy aromatic solvent marketed by AMOCO Chemicals Corp., Chicago, Ill. This solvent has a specific gravity, at 60°/60° F., of 0.982; it contains 93% aromatics and has a mixed aniline point of 64° F.

The method and compositions of the present invention as well as the results achieved with their use are further illustrated in the following examples.

EXAMPLE 1

Evaluation of
N-(1-Ethylpropyl)-2,6-dinitro-3,4-xylidine;
Methyl-o-(5-isopropyl-5-methyl-4-oxo-2-imidazolin-2-yl)benzoate and combination treatments thereof as Pre-emergence Weed Control Agents in Rice Paddies In order to determine the effectiveness of combination treatments, utilizing from about 0.45 to 1.35 kg per hectare of N-(1-ethylpropyl)-2,6-dinitro-3,4-xylidine and from 0.36 to 1.08 kg per hectare of methyl-o-(5-isopropyl-5-methyl-4-oxo-2-imidazolin-2-yl)benzoate, for the selective preemergence control of undesirable weed species in the presence of paddy rice, conventional rice paddies having a history of heavy infestation of *Echinochloa crus-galli* (E.c.), *Cyperus difformis* (C.d.), *Monochoria vaginalis* (M.v.), *Rotala indica* (R.i.), *Lindernia pyxidaria* (L.p.), *Eleocharis acicularis* (E.A.), *Scirpus hotarui* (S.h.), *Sagittaria pygmoea* (S.p.), *Cyperus serotinus* (C.s.), and *Elatine triandra* (E.t.), were selected for the tests. The paddies are filled with water and puddled (i.e. the mud stirred up) to bring weed seeds to the surface. Paddies are randomly divided into 3 groups for (1) spraying 3 days before transplanting (3DBT) of the rice; (2) spraying 3 days after transplanting (3DAT) of the rice, and (3) spraying 7 days after transplanting (7DAT) of the rice.

Formulations used in these tests are as follows:

Emulsifiable Concentrate (I)

25% by weight, Methyl-o-(5-isopropyl-5-methyl-4-oxo-2-imidazolin-2-yl)benzoate.
10% by weight, nonionic emulsifier (T-mulz 339- Manufactured by Thompson Hayward).
15% by weight, heavy aromatic solvent, 93% aromatics, mixed aniline point 64(18° C.), Flash point 180(82° C.). (PANASOL AN-2 Amoco Chemicals, Chicago Ill.).
50% by weight, Cyclohexanone.

Emulsifiable Concentrate (II)

32.32% by weight, 93% (tech) N-(1-Ethylpropyl)-2,6-dinitro-3,4-xylidine.
3.3% by weight, anionic-nonionic emulsifer (ATLOX 3404F I.C.I. United States)
2.7% by weight, anionic-nonionic emulsifier (ATLOX 3403F I.C.I. United States)
61.68% by weight, heavy aromatic solvent, 93% aromatics, mixed aniline point 64(18° C.), Flash Point 180(82° C.) (PANASOL AN-2 Amoco Chemicals, Chicago, Ill.

Three days before transplanting of the lowland rice plants separate paddies are sprayed with an aqueous suspension of the emulsifiable concentrate (I), in sufficient quantity to provide 0.48 kg/ha, 0.96 kg/ha or 1.44 kg/ha of methyl-o-(5-isopropyl-5-methyl-4-oxo-2-imidazolin-2-yl)benzoate or with a combination treatment of the emulsifiable concentrates I and II, in sufficient amount to provide 0.45, 0.9 or 1.35 kg per hectare of N(1-ethylpropyl-2,6-dinitro-3,4-xylidine, in combination with, 0.36, 0.72 or 1.08 kg per hectare, respectively, of Methyl-o-(5-isopropyl-5-methyl-4-oxo-2-imidazolin-2-yl)benzoate. After transplanting of the rice plants, paddies are cared for using controlled irrigation and examined periodically.

Thirty one days after transplanting paddies are examined to evaluate the weed control achieved. The paddies are rated on a weed control index in which a 0 rating equals no control and a 9 rating indicates complete weed kill. Partial control of weeds is indicated by assignment of integers between 0 and 9. Ratings were determined by harvesting the weeds in each plot, separating them by species and drying and weighing said weeds.

Plots sprayed 3 or 7 days after transplanting of the rice are cared for and rated in the same manner as described for plots treated 3 days before transplanting (3DBT). Data obtained are reported below, where it can be seen that the combination treatment of N-(1-Ethylpropyl)-2,6-dinitro-3,4-xylidine and methyl-o-(5-isopropyl-5-methyl-4-oxo-2-imidazolin-2-yl)benzoate gave excellent control of *Echinochloa crus-galli, Cyperus difformis, Monochoria vaginalis, Rotala indica, Lindernia pyxidaria, Eleocharis acicularis* and *Elatine triandra*, at all combination rates tested. The data also shows complete control, or virtually complete control, of *Scirpus hotarui* and *Cyperus serotinus* with the combination treatments of 0.90 to 1.35 kg/ha of N-(1-ethylpropyl)-2,6-dinitro-3,4-xylidine with 0.72 to 1.08 kg/ha of methyl-o-(5-isopropyl-5-methyl-4-oxo-2-imidazolin-2-yl) benzoate, applied 3 days after transplanting (3DAT).

TABLE I

Preemergence Herbicidal Activity of Test Chemicals and Compositions against Weed Species Found in Paddy Rice

| Compound or Composition | Rate kg/ha | Annual Weeds | | | | | | Perennial Weeds | | | |
|---|---|---|---|---|---|---|---|---|---|---|---|
| | | Grass | | Broadleaf | | | | | | | |
| | | E.c. | C.d. | M.v. | R.i. | L.p. | E.t. | E.a. | S.h. | S.p. | C.s. |
| Methyl-o-(5-iso-propyl-5-methyl-4-oxo-2-imidazolin-2-yl)benzoate | (3DBT) | | | | | | | | | | |
| | 0.48 | 1 | 1 | 7 | 7 | 1 | 1 | 1 | 1 | 1 | 3 |
| | 0.96 | 1 | 1 | 8 | 7 | 1 | 1 | 5 | 1 | 1 | 7 |
| | 1.44 | 1 | 1 | 8 | 8 | 1 | 1 | 7 | 1 | 3 | 9 |
| | (3DAT) | | | | | | | | | | |
| | 0.48 | 1 | 1 | 7 | 1 | 1 | 1 | 7 | 1 | 3 | 7 |
| | 0.96 | 1 | 3 | 8 | 7 | 1 | 7 | 7 | 1 | 3 | 9 |
| | 1.44 | 1 | 7 | 8 | 7 | 1 | 8 | 9 | 3 | 3 | 8 |
| | (7DAT) | | | | | | | | | | |
| | 0.48 | 1 | 1 | 7 | 7 | 1 | 1 | 7 | 1 | 3 | 3 |
| | 0.96 | 1 | 1 | 8 | 8 | 1 | 1 | 7 | 1 | 3 | 5 |
| | 1.44 | 1 | 1 | 8 | 8 | 1 | 5 | 9 | 1 | 3 | 5 |
| N—(1-Ethylpropyl)-2,6-dinitro-3,4-xylidine | (3DBT) | | | | | | | | | | |
| | 0.45/0.36 | 9 | 9 | 9 | 9 | 9 | 9 | 9 | 3 | 1 | 7 |
| | 0.96/0.72 | 9 | 9 | 9 | 9 | 9 | 9 | 9 | 5 | 3 | 9 |
| | 1.35/1.08 | 9 | 9 | 9 | 9 | 9 | 9 | 9 | 8 | 5 | 9 |
| Methyl-o-(5-iso-propyl-5-methyl-4-oxo-2-imidazolin-2-yl)benzoate | (3DAT) | | | | | | | | | | |
| | 0.45/0.36 | 9 | 9 | 9 | 9 | 9 | 9 | 9 | 3 | 5 | 7 |
| | 0.9/0.72 | 9 | 9 | 9 | 9 | 9 | 9 | 9 | 8 | 5 | 9 |
| | 1.35/1.08 | 9 | 9 | 9 | 9 | 9 | 9 | 9 | 8 | 5 | 9 |
| | (7DAT) | | | | | | | | | | |
| | 0.45/0.30 | 9 | 9 | 9 | 9 | 9 | 9 | 9 | 4 | 1 | 1 |
| | 0.9/0.72 | 9 | 9 | 9 | 9 | 9 | 9 | 9 | 7 | 5 | 3 |
| | 1.35/1.08 | 9 | 9 | 9 | 9 | 9 | 9 | 9 | 7 | 5 | 5 |

TABLE I-continued

Preemergence Herbicidal Activity of Test Chemicals and Compositions against Weed Species Found in Paddy Rice

| Compound or Composition | Rate kg/ha | Ratings 31 Days After Transplanting | | | | | | | | | |
|---|---|---|---|---|---|---|---|---|---|---|---|
| | | Annual Weeds | | | | | | Perennial Weeds | | | |
| | | Grass | | Broadleaf | | | | | | | |
| | | E.c. | C.d. | M.v. | R.i. | L.p. | E.t. | E.a. | S.h. | S.p. | C.s. |
| Untreated Check | — | (229) | (8.9) | (419) | (24.3) | (0.7) | (1.8) | (1.6) | (1.5) | (2.2) | (5.6) |

(3DBT) = 3 days before transplanting
(3DAT) = 3 days after transplanting
(7DAT) = 7 days after transplanting
Figures in Parenthesis showed = Dry weight of each weed (g/m²)

EXAMPLE 2

Evaluation of N-(1-Ethylpropyl)-2,6-dinitro-3,4-xylidine; Methyl-o-(5-isopropyl-5-methyl-4-oxo-2-imidazolin-2-yl) benzoate and combination treatments thereof as preemergence weed control agents in rice paddies.

The procedure of Example 1 above was employed in the present evaluation. Experimental plots were selected that had a history of heavy infestation of *Echinochloa crus-galli; Cyperus difformis; Lindernia pyxidaria; Jussiaea prostrata; Rotala indica* and *Eclipta alba*. Since the selected plots are not known to have had heavy infestations of *Scirpus hotarui* or *Cyperus serotinus*, additional plots with a history of heavy infestations of these weed species are also selected for these evaluations.

The N-(1-ethylpropyl)-2,6-dinitro-3,4-xylidine formulation used in these tests is a dilute aqueous spray of a 32.32% by weight emulsifiable concentrate. The formulation is identified as "emulsifiable concentrate II" in example 1.

The Methyl-o-(5-isopropyl-5-methyl-4-oxo-2-imidazolin-2-yl)benzoate used in these tests is a dilute aqueous spray of a wettable powder formulation prepared by thoroughly blending 55.55% by weight of methyl-o-(5-isopropyl-5-methyl-4-oxo-2-imidazolin-2-yl)benzoate; 3% by weight of a sugar free, sodium based sulfonate of Kraft lignin dispersing agent, having 1 mole sulfonation per mole of lignin (Polyfon O Manufactured by Westvaco-Polychemicals); 1.0% by weight of sodium N-methyl-N-oleoyltaurate, wetting agent (Igepon T-77 GAF Corp. Chemical Products); and 40.45% by weight of attapulgite. The blended composition is then air milled to an average particle size of <1.2μ. The method of rating the weed control achieved and the index employed in such rating are the same as defined in Example 1, above. Data obtained are reported in table II below were it can be seen that superior control of the several weed species employed in these tests is achieved with the combination of 0.75 to 1.25 kg/ha of N-(1-ethylpropyl)-2,6-dinitro-3,4-xylidine and from 0.75 to 1.0 kg/ha of methyl-o-(5-isopropyl-5-methyl-4-oxo-2-imidazolin-2-yl)benzoate, applied 3 days after transplanting of the rice.

TABLE II

Evaluation of Test Compounds and Compositions for Preemergence Control of undesirable Weed Species in Paddy Rice

| Compound or Composition | Rate kg/ha | Rating 4 Months After Transplanting | | | | | | | | |
|---|---|---|---|---|---|---|---|---|---|---|
| | | Annual Weeds | | | | | | Perennial Weeds | | |
| | | Grass | | Broadleaf | | | | | | |
| | | E.c. | C.d. | L.p. | J.p. | R.i. | E.al. | S.p. | S.h.* | C.s.* |
| N—(1-Ethylpropyl)- 2,6-dinitro- 3,4-xylidine | (3DBT) | | | | | | | | | |
| | 0.75 | 8 | 0 | 0 | 0 | 8 | 4 | 0 | 0 | 0 |
| | 1.0 | 8 | 7 | 6 | 8 | 9 | 9 | 4 | 1 | 0 |
| | 1.25 | 8 | 0 | 6 | 0 | 0 | 5 | 0 | 1 | 0 |
| | (3DAT) | | | | | | | | | |
| | 0.75 | 7 | 5 | 4 | — | 5 | 8 | 0 | 0 | 1 |
| | 1.0 | 8 | 8 | 8 | — | 9 | 9 | 6 | 0 | 1 |
| | 1.25 | 9 | 6 | 7 | — | 4 | 8 | 0 | 4 | 4 |
| N—(1-Ethylpropyl)- 2,6-dinitro-3,4- xylidine/ Methyl-o-(5-iso- propyl-5-methyl- 4-oxo-2-imida- zolin-2-yl) benzoate | (3DBT) | | | | | | | | | |
| | 0.5/0.5 | 8 | 9 | 7 | 9 | 9 | 6 | 9 | 0 | 5 |
| | 0.5/0.75 | 8 | 9 | 5 | 9 | 9 | 1 | 8 | 0 | 4 |
| | 0.5/1.0 | 8 | 9 | 8 | 9 | 9 | 9 | 9 | 0 | 0 |
| | 0.75/0.5 | 8 | 9 | 7 | 9 | 9 | 9 | 8 | 0 | 3 |
| | 0.75/0.75 | 8 | 9 | 6 | 9 | 9 | 9 | 8 | 4 | 3 |
| | 0.75/1.0 | 8 | 9 | 7 | 9 | 9 | 9 | 8 | 0 | 3 |
| | 1.0/0.5 | 8 | 9 | 8 | 9 | 9 | 9 | 9 | 4 | 2 |
| | 1.0/0.75 | 8 | 9 | 8 | 9 | 9 | 9 | 8 | 3 | 0 |
| | 1.0/1.0 | 8 | 9 | 7 | 9 | 9 | 9 | 8 | 0 | 0 |
| | 1.25/0.5 | 8 | 9 | 8 | 9 | 9 | 9 | 8 | 1 | 0 |
| | 1.25/0.75 | 8 | 9 | 2 | 9 | 9 | 9 | 8 | 1 | 1 |
| | 1.25/1.0 | 8 | 9 | 8 | 9 | 9 | 9 | 8 | 5 | 0 |
| N—(1-Ethylpropyl)- 2,6-dinitro-3,4- xylidine/ Methyl-o-(5-iso- propyl-5-methyl- 4-oxo-2-imidaz- olin-2-yl)benzoate | (3DAT) | | | | | | | | | |
| | 0.5/0.5 | 8 | 9 | 7 | — | 9 | 8 | 9 | 0 | 1 |
| | 0.5/0.75 | 8 | 9 | 5 | — | 9 | 9 | 9 | 5 | 8 |
| | 0.5/1.0 | 8 | 9 | 7 | — | 9 | 9 | 9 | 5 | 8 |
| | 0.75/0.5 | 8 | 9 | 8 | — | 9 | 9 | 9 | 2 | 0 |
| | 0.75/0/75 | 7 | 9 | 8 | — | 9 | 8 | 9 | 5 | 8 |
| | 0.75/1.0 | 5 | 9 | 8 | — | 9 | 8 | 9 | 5 | 7 |
| | 1.0/0.5 | 8 | 9 | 8 | — | 9 | 9 | 9 | 3 | 0 |
| | 1.0/0.75 | 8 | 9 | 6 | — | 9 | 8 | 9 | 5 | 8 |

TABLE II-continued

Evaluation of Test Compounds and Compositions for Preemergence Control of undesirable Weed Species in Paddy Rice

| Compound or Composition | Rate kg/ha | Rating 4 Months After Transplanting | | | | | | | | |
|---|---|---|---|---|---|---|---|---|---|---|
| | | Annual Weeds | | | | | | Perennial Weeds | | |
| | | Grass | | Broadleaf | | | | | | |
| | | E.c. | C.d. | L.p. | J.p. | R.i. | E.al. | S.p. | S.h.* | C.s.* |
| | 1.0/1.0 | 8 | 9 | 9 | — | 9 | 8 | 9 | 5 | 5 |
| | 1.25/0.5 | 8 | 9 | 4 | — | 9 | 9 | 9 | 6 | 8 |
| | 1.25/0.75 | 8 | 9 | 8 | — | 9 | 8 | 8 | 7 | 8 |
| | 1.25/1.0 | 9 | 9 | 8 | — | 9 | 9 | 9 | 7 | 8 |
| Untreated Check | — | (705) | (10.1) | (0.8) | (0.6) | (0.4) | (1.1) | (26.5) | (5.8) | (7.2) |

\* = Data obtained for these weed species in a different test.
Figures in parethesis showed: Fresh weight of weeds (g/m$^2$)
J.p. = *Jussiaea prostrata*
E.al. = *Eclipta alba*

EXAMPLE 3

Evaluation of test compositions for the selective control of undesirable weeds in the presence of paddy rice and the simultaneous enhancement of rice yields from the treated paddies In the following tests rice paddies with histories of heavy infestations of weeds such as *Echinochloa crusgalli; Scirpus hotarui; Lindernia pyxidaria; Elatine triandra; Rotala indica; Monochoria vaginalis; Cyperus serotinus; Sagittaria pygmoea; Cyperus difformis; Justicia procumbeus* and *Eclipta alba* are selected.

The paddies which are to be used are puddled and then planted with one month old rice plants. Three days after the transplanting of the rice, the paddies are sprayed with dilute aqueous solutions of the emulsifiable concentrates I and II defined in Example 1, above. Sufficient spray is applied to provide 1 kg/hectare of N-(1-ethylpropyl)-2,6-dinitro-3,4-xylidine and either 0.5 or 0.75 kg/hectare of methyl-o-(5-isopropyl-5-methyl 4-oxo-2-imidazolin-2-yl)benzoate. The paddies are treated by controlled irrigation and the paddies examined periodically to evaluate weed control. After 4 months the paddies are harvested. Weed control is determined by separating the weeds by species and determining the dry weed weight. Rice yield is determined by weighing the harvested rice. Untreated controls are harvested for weeds and rice and the percent weed control calculated against the untreated checks. Similarly, rice yield is determined against the yield obtained in the untreated check and reported as percent rice yield over control.

From the data obtained it can be seen that rice yield with both combinations of 1 kg/hectare of N-(1-ethylpropyl)-2,6-dinitro-3,4-xylidine with either 0.5 or 0.75 kg/hectare of methyl-o-(5-isopropyl-5-methyl-4-oxo-2-imidazolin-2-yl)benzoate, gave a yield enhancement of from 116% to 125% over untreated controls and excellent control of nearly all weed species.

TABLE III

Evaluation of Herbicidal Combinations for Weed Control and Crop Yield in Paddy Rice, reported as % Weed Control and % of Crop Yield over Controls
Combination Treatments Appplied 3 Days After Transplanting (3DAT). Harvested 116(DAT)

| Combination Rates Kg. ai/ha | Weed Species | | | | | | | Paddy Rice |
|---|---|---|---|---|---|---|---|---|
| | *Echinochloa crus-galli* | *Scirpus hotarui* | *Lindernia pyxidaria* | *Elatine triandra* | *Rotala indica* | *Monochoria vaginalis* | *Cyperus serotinus* | % of Yield Over Control |
| A+B | | | | | | | | |
| 1.0 + 0.5 | 100% | 30% | 85% | 85% | 85% | 85% | 0% | 118% |
| 1.0 + 0.75 | 100% | 50% | 100% | 100% | 100% | 100% | 80% | 118% |
| | *Echinochloa crus-galli* | *Sagittaria pygmaea* | *Lindernia pyxidaria* | *Cyperus difformis* | *Justicia procumbens* | *Rotala indica* | *Eclipta alba* | % of Yield Over Control |
| 1.0 + 0.75 | 85% | 100% | 60% | 100% | 100% | 100% | 85% | 125% |
| 1.0 + 0.50 | 80% | 100% | 80% | 100% | 100% | 100% | 100% | 116% |
| 1.0 + 0.75 | 80% | 100% | 60% | 100% | 100% | 100% | 80% | 125% |

A = N—(1-Ethylpropyl)-2,6-dinitro-3,4-xylidine
B = Methyl-o-(5-isopropyl-5-methyl-4-oxo-2-imidazolin-2-yl)benzoate

EXAMPLE 4

Evaluation of N-(1-Ethylpropyl)-2,6-dinitro-3,4-xylidine and Methyl-o-(5-isopropyl-5-methyl-4-oxo-2-imidazolin-2-yl)benzoate, applied singly or in combination on transplanted rice and weeds, data taken at Harvest 4 months after transplanting In these tests, rice paddies having a history of heavy infestation of *Echinochloa crus-galli* and *Monochoria vaginalis* are selected. The paddies are puddled, planted with one month old rice seedlings and three days after transplanting, sprayed with a dilute aqueous spray(s) containing the test compounds. The formulations utilized are the emulsifiable concentrates I and II, described in Example 1 above.

The paddies are maintained by continuous flood throughout the 4 month growing season.

Four months after transplanting, rice and weeds are harvested from all plots. The rice and weeds are separated, weighed and the results recorded. Obtained data are reported in table IV below, where it can be seen that the paddy treated with 1.0 kg/hectare of N-(1-ethylpropyl)-2,6-dinitro-3,4-xylidine and 0.5 kg/ hectare of methyl-o-(5-isopropyl-5-methyl-4-oxo-2-imidazolin-2-yl)benzoate, is totally free of *Echinochloa crus-galli* and *Monochoria vaginalis*. Moreover, the paddy receiving this preferred treatment produced 7.1 tons per hectare of rice; whereas, the greatest yield from all other paddy treatments is 5.8 tons per hectare.

It is noted that complete control of *Echinochloa* and *Monochoria*, coupled with a better than 18% enhancement of rice yield are attained.

TABLE IV

Effect of Preemergence Spray of N—(1-Ethylpropyl)-2,6-dinitro-3,4-xylidine and Methyl-o-(5-isopropyl-5-methyl-4-oxo-2-imidazolin-2-yl)benzoate applied singly or in combination on Transplanted Rice and Weeds, data taken at harvest 4 months after transplanting

| | | Rated 4 Months After Transplanting | | | |
|---|---|---|---|---|---|
| | | Fresh Weed Weight | | | |
| Compound | Rate kg/ha | E.c. (t/ha) | M.v. (t/ha) | Total (t/ha) | Rice Yield (t/ha) |
| Methyl-o-(5-isopropyl-5-methyl-4- | 0.5 | 24.4 | 0 | 24.4 | 2.6 |
| oxo-2-imidazolin-2-yl)benzoate | 1.0 | 32.4 | 0 | 32.4 | 1.2 |
| N—(1-Ethylpropyl)-2,6-dinitro- | 0.5 | 0.4 | 1.7 | 2.1 | 5.2 |
| 3,4-xylidine | 1.0 | 0.3 | 5.0 | 5.3 | 4.7 |
| | 1.5 | 0.2 | 1.3 | 1.5 | 5.8 |
| N—(1-Ethylpropyl)-2,6-dinitro- | 0.5 + 0.75 | 1.0 | 0 | 1.0 | 5.2 |
| 3,4-xylidine-plus- | 0.5 + 1.0 | 0.5 | 0 | 0.5 | 5.0 |
| | 0.75 + 0.5 | 1.6 | 0 | 1.6 | 5.6 |
| Methyl-o-(5-isopropyl-5-methyl- | 0.75 + 0.75 | 1.2 | 0 | 1.2 | 5.3 |
| 4-oxo-2-imidazolin-2-yl)- | 0.75 + 1.0 | 0.2 | 0 | 0.2 | 5.2 |
| benzoate | 1.0 + 0.5 | 0 | 0 | 0 | 7.1 |
| | 1.0 + 0.75 | 0.6 | 0 | 0.6 | 5.4 |

Example 5

Evaluation of N-(1-ethylpropyl)-2,6-dinitro-3,4-xylidine; sodium-o-(5-isopropyl-5-methyl-4-oxo-2-imidazolin-2-yl) benzoate and synergistic combination treatments as pre-emergence weed control agents and yield enhancing agents in rice The following tests were conducted to determine the effectiveness of test compositions for synergistically enhancing rice yields and simultaneously controlling undesirable plant species in drill seeded rice paddies. In these tests, rain soaked ricespaddies, with soil containing 17% organic matter and a history of heavy infestations of *Ageratum conyzoides, Ludwigia suffruticosa, Drymaria cordata, Eclipta alba, Polygonum acre, Galinsoga parviflora, Portulaca oleracea, Brachiaria purpuracens, Digitaria sanguinalis, Echinochloa colonum* and *Commelina nudiflora*, were drill seeded with rice. A randomized complete block design was employed using 2 m × 5 m plots and 4 replications per treatment. The plots were sprayed, 0 to 2 days following seeding, with aqueous suspensions of test compound(s) applied at the rate of 200 l/ha. Six hours after the test plots were sprayed, heavy rains fell. The plots were examined periodically from planting to harvest and observations recorded. Twenty five days after planting it was noted that average rice germination in the test plots was 90%. Thirty days after seeding all plots were examined and weed control noted for each plot. Data obtained are reported in table V below where it can be seen that excellent control of undesirable weeds is obtained with the compositions of choice.

Four months after planting the rice is harvested in each plot. Yield data for each plot is reported in Table VI below where it can be seen that the compositions of the present invention synergistically enhanced rice yields.

TABLE V

| | Evaluation of Compounds and Compositions as Herbicidal Agents | | | | | | | | | | | |
|---|---|---|---|---|---|---|---|---|---|---|---|---|
| Compound or | Dosage | % Control of Weed Species | | | | | | | | | | |
| Composition | kg/ha | A.c. | D.c. | E.a. | G.p. | L.s. | P.a. | P.o. | B.p. | D.s. | E.c. | C.m. |
| Sodium-o-(5-isopropyl-5- | 0.50 | 80 | 90 | 90 | 80 | 100 | — | 100 | 30 | 30 | 40 | 10 |
| methyl-4-oxo-2-imidazolin- | 0.75 | 90 | 100 | 80 | 90 | 100 | — | 100 | 30 | 40 | 60 | — |
| 2-yl)benzoate | | | | | | | | | | | | |
| N—(1-Ethylpropyl)-2,6- | 1.75 | 10 | 100 | 80 | 30 | 70 | 30 | — | 30 | 70 | 70 | 0 |
| dinitro-3,4-xylidine | | | | | | | | | | | | |
| N—(1-Ethylpropyl)-2,6- | 1.50 + 0.50 | 80 | 100 | 90 | 80 | 100 | 100 | 100 | 40 | 50 | 70 | 100 |
| dinitro-3,4-xylidine | | | | | | | | | | | | |
| Plus | | | | | | | | | | | | |
| Sodium-o-(5-isopropyl-5- | 1.75 + 0.50 | 90 | 100 | 90 | 90 | 100 | 100 | 100 | 80 | 80 | 90 | — |
| methyl-4-oxo-2-imidazolin- | | | | | | | | | | | | |
| 2-yl)benzoate | | | | | | | | | | | | |
| Untreated Check** | — | (75) | (368) | (9) | (13) | (243) | (6.5) | (05) | (8) | (28) | (4) | (2) |

** = Average number of weeds/sq. m
A.c. = *Ageratum conyzoides*
D.c. = *Drymaria cordata*
E.a. = *Eclipta alba*
G.p. = *Galinsoga Parviflora*
L.s. = *Ludwigia suffruticosa*
P.a. = *Polygonum acre*
P.o. = *Potulaca oleracea*
B.p. = *Brachiaria purpuracens*
D.s. = *Digitaria sangiunalis*
E.c. = *Echinochloa colonum*
C.m. = *Commelina nudiflora*

TABLE VI

Evaluation of Compounds and Compositions for Increase Rice Yields

| Compound or Composition | Average Rice Yield, Four Replicates. | | |
|---|---|---|---|
| | Dosage kg/ha | Yield kg/ha | % Over Weeded Check |
| Sodium-o-(5-isopropyl-5-methyl-4-oxo-2-imidazolin-2-yl)benzoate | 0.50 | 6,219 | 45.1 |
| | 0.75 | 6,271 | 46.3 |
| N—(1-Ethylpropyl)-2,6-dinitro-3,4-xylidine | 1.75 | 5,012 | 16.9 |
| N—(1-Ethylpropyl)-2,6-dinitro-3,4-xylidine Plus Sodium-o-(5-isopropyl-5-methyl-4-oxo-2-imidazolin-2-yl)benzoate | 1.50 + 0.50 | 7,261 | 69.4 |
| | 1.75 + 0.50 | 7,482 | 74.6 |
| Hand Weeded Check | — | 4,286 | — |

We claim:

1. A method for synergistically enhancing the yield of rice from irrigated or flooded paddies and simultaneously controlling undesirable annual and perennial weeds in the presence of said rice crop comprising: applying to the locus in which said rice is grown, 0 to 2 days after drill seeding said locus with rice or 3 to 7 days after said crops are transplanted to the growing area, about 1.75 kg/hectare of N-(1-ethylpropyl)-2,6-dinitro-3,4-xylidine and about 0.50 kg/hectare of sodium-o-(5-isopropyl-5-methyl-4-oxo-2-imidazolin-2-yl)-benzoate.

2. A method for simultaneously increasing rice yields and selectively controlling *Ageratum conyzoides, Drymaria cordata, Galinsoga parviflora, Ludwigia suffruticosa, Polygonum acre, Commelina nudiflora, Monochoria vaginalis, Elatine triandra, Eleocharis acicularis, Lindernia pyridaria, Rotala indica, Echinochloa crusgalli, Cyperus difformis, Jussiaea prostrata, eclipta alba, Sagittaria pygamaea, Cyperus serotinus* and *Scirpus hotarui,* in the presence of paddy rice, comprising: applying to drill seeded rice paddies 0 to 2 days after seeding or to paddies in which said rice has been transplanted 3 to 7 days before treatment, a sufficient quantity of dilute aqueous spray containing:
(a) N-(1-ethylpropyl)-2,6-dinitro-3,4-xylidine and
(b) sodium-o-(5-isopropyl-5-methyl- 4-oxo-2-imidazolin-2-yl)benzoate and an emulsifying agent, to provide about 1.75 kg/hectare of said xylidine compound and about 0.5 kg/hectare of said benzoate compound whereby the growth of the above-said weed species is inhibited and the rice yield is increased.

3. A method according to claim 2 wherein said xylidine and benzoate compounds are applied separately or in admixture in the form of a dilute aqueous spray containing an emulsifying agent of nonionic or anionic/-nonionic emulsifying agents.

* * * * *